United States Patent [19]

Kim et al.

[11] Patent Number: 5,447,961
[45] Date of Patent: Sep. 5, 1995

[54] O/W TYPE EMULSION CONTAINING MILK

[75] Inventors: Young D. Kim, Seoul; Byung J. Ha, Ansan; Young S. Park, Kyungki-do, all of Rep. of Korea

[73] Assignee: Pacific Corporation, Seoul, Rep. of Korea

[21] Appl. No.: 200,280

[22] Filed: Feb. 23, 1994

[30] Foreign Application Priority Data

Apr. 8, 1993 [KR] Rep. of Korea ............... 1993-5875

[51] Int. Cl.$^6$ .................................................. A61K 9/12
[52] U.S. Cl. ..................................... 424/535; 514/458; 514/775; 514/938
[58] Field of Search ................... 514/775, 458, 938

[56] References Cited

U.S. PATENT DOCUMENTS

| | | | |
|---|---|---|---|
| 2,023,125 | 12/1935 | Dryfuss et al. | 514/775 |
| 3,340,153 | 9/1967 | Kast et al. | 514/775 |
| 3,959,491 | 5/1976 | Young et al. | 514/775 |
| 4,994,496 | 2/1991 | Repasky et al. | 514/775 |
| 5,235,073 | 8/1993 | Kim et al. | 549/408 |
| 5,250,289 | 10/1993 | Boothroyd et al. | 514/938 |
| 5,302,376 | 4/1994 | Forestier et al. | 514/938 |

FOREIGN PATENT DOCUMENTS

| | | | |
|---|---|---|---|
| 2631824 | 12/1989 | France | 424/195 |
| 0085808 | 5/1983 | Japan | 514/458 |

OTHER PUBLICATIONS

The Merck Index, 1976, 9th Edition, pp. 1221 and 1222.

Primary Examiner—Dale R. Ore
Attorney, Agent, or Firm—Nixon & Vanderhye

[57] ABSTRACT

Disclosed herein is an O/W type emulsion comprising oils and milk characterized in that which comprises as an emulsifier polyethoxylated vitamin E in amount of 0.01 to 10% by weight. This emulsion may further contain vitamin E or its derivative.

The emulsion according to the invention may stored for a long period of time without phase separation because polyethoxylated vitamin E contained therein forms microspheres in the interface of each emulsion particles. Further, it shows an improved activity of protecting the skin from the harmful oxygen species.

4 Claims, No Drawings

O/W TYPE EMULSION CONTAINING MILK

BACKGROUND OF THE INVENTION

1. Field of the Invention

The invention relates to an oil in water(O/W) type emulsion containing milk and, more specifically relates to an O/W type emulsion comprising milk, oils and polyethoxylated vitamin E, which can be stored for a long period of time without a phase separation.

2. Description of the Prior Art

Milk, which is one of the most nutrient-rich food, is also an useful material for cosmetic compositions because it smooths the skin and can prevent dryness when it applied onto the skin. Further, while milk is a nearly complete food which contains most of nutrients required for human being, for example proteins, fats, vitamins, minerals, phospolipid and other components, it is easily available due to its plentiful production and low price.

A milk protein, iniferin mainly composed of glycoprotein lactoperin has been used as a material for cosmetics since it is capable of preventing freckle and scavenging harmful oxygen species.

However, milk itself is not a useful material for cosmetics because it undergoes oxidation and hydrolysis, causing putrefaction and malodor when preserved for a long period of time. Further, milk must be diluted with water and other suitable solvent when employed for cosmetics and this dilution can promote hydrolysis of milk and acidification of unsaturated triglycerides in milk by air, particularly harmful oxygens.

Moreover, since proteins in milk are precipitated under the acidic condition, cosmetic compositions which usually are rather acidic cannot stably stored when incorporated with milk.

Under these circumstances, the present inventors had made extensive researches to solve the above-mentioned problems and to provide a cosmetic composition which contains milk and can be stored for a long period time, and a result thereof have accomplished the present invention.

SUMMARY OF THE INVENTION

Therefore, one object of the invention is to provide a cosmetic composition comprising milk which can be stored for a long period of time.

Another object of the invention is to provide an O/W type emulsion comprising oils and milk characterized in that which comprises as an emulsifier polyethoxylated vitamin E in amount of 0.01 to 10% by weight.

Another object of the invention is to provide an O/W type emulsion comprising oils and milk characterized in that which comprises polyethoxylated vitamin E and vitamin E or vitamin E acetate.

DETAILED DESCRIPTION OF THE INVENTION

The emulsion of the invention comprises as an emulsifier polyethoxylated vitamin E in order to emulsifying milk with oils without a phase separation for a prolonged period of time.

Polyethoxylated vitamin E is disclosed in U.S. Pat. No. 5,235,037 issued to the applicant and may be prepared by the methods disclosed in the above patent. This compound can be safely applied to the skin of human being and shows excellent moisture retention and surface action activities.

In emulsion, the particles continuously move and collide with each other. At the time of colliding with each other, the particles may be united, resulting in unstabilization of file emulsion. If there are formed microspheres at the interface between the emulsion particles, the emulsion become very stable since the viscosity around the particles is very high and the unification of particles collide with each other is prohibited.

Polyethoxylated vitamin E employed in the present invention are highly tend to adhere to the interface between emulsion particles and form a more compact interface layer compared with the conventional emusifiers which are usually employed in the cosmetics. The more compact interface layer may be formed because polyethoxlyated vitamin E form microspheres near the interface between emulsion particles. This formation of microspheres makes it possible for an emulsion to be become more stable.

Further, polyethoxylated vitamin E can stabilize the components of the milk in the emulsion as well as may serve as a barrier to maintain the water content of the stratum corneum when applied onto the skin.

The emulsion of the present invention containing milk and polyethoxylated vitamin E exhibits a synergistic effect in scavenging harmful oxygen species such as singlet oxygen. This action of scavenging harmful oxygens is improved when vitamin E or its ester, for example vitamin E acetate, which has known to show excellent antioxidant activity, is incorporated into the emulsion.

The emulsion of the present invention is in the form of oil-in-water(O/W) emulsion and therefore it does not easily undergo phase separation when diluted with water compared with water-in-oil(W/O) emulsion. The other feature of the present invention is to provide a low viscous emulsion which has a viscosity of less than 100 cps, especially in milky lotion and does not undergo phase separation for a long period of time.

Polyethoxylated vitamin E may be any one of those one which contain average 5 to 15 moles of ethylene oxide in the molecule and can be employed in single or combination. The mount of polyethoxylated vitamin E contained in the emulsion may be varied between 0.01% by weight and 10% by weight and preferably is 0.1 to 1% by weight. The ratio of polyethoxylated vitamin E to milk is 1:1 to 1:10 in terms of part by weight.

The emulsion may further contain natural or synthetic vitamin E or its esters such as vitamin E acetate. The mount of vitamin E or its ester contained in the emulsion may be varied between 0.01% by weight and 10% by weight and preferably is 0.1 to 1% by weight.

Milk employed in the emulsion of the invention may be any one of powdered whole milk (full fat milk), powdered skimmed milk or intact milk and preferably is an intact milk sterilized by UV radiation.

Oils employed in the emulsion of the invention are any one usually employed in the cosmetics and may include, but not intended to be limited thereto, liquid paraffin, isopropyl myristate or squalene and preferably is liquid paraffin.

The ratio of the oil components to the aqueous components is 2:3 to 1:10 in terms of part by weight.

The emulsion of the invention may contain moisturizers, physiologically active substances and preservatives, all of which are well known to and can be selected without problem by those who skilled in the art.

The emulsion of the invention can be prepared by conventional methods. For example, oil components such as oils, polyethoxylated vitamin E and other vitamin E derivatives and aqueous components such as moisturizers and water are each heated to 70°–80° C. and the oil part is gradually added to the aqueous part. The mixture is homogeneously mixed at 7,000–9,000 rpm for about 3–10 minutes to give a emulsion. Then, preservative, perfume and other physiologically active ingredients are added and the mixture is again homogeneously mixed at 50°–60° C. After foams are removed under vacuum and the emulsion is cooled to 20°–30° C.

PREFERRED EMBODIMENTS OF THE INVENTION

The present invention shall be illustrated in more detail by way of the following Examples. The following Examples are merely illustrative and it should be understood that the present invention is not limited to these Examples.

EXAMPLES 1-2 and COMPARATIVE EXAMPLES 1-2

Aqueous components 1, 2 and 8 and oil components 3 to 7 as shown in Table 1 were heated to 75° C. to give fluids respectively and the oil part were dispersed into the aqueous part. The mixture was well mixed with a agitator and cooled to room temperature to give a O/W type emulsions such as a low viscous milky lotion.

The viscosity of each emulsion was measured using Brooked viscometer and the results are shown in Table 1.

TABLE 1

| Components | | Example | | | |
|---|---|---|---|---|---|
| | | Ex. 1 | Ex. 2 | Comp.Ex.1 | Comp.Ex.2 |
| 1. | Purified water | up to 100 | up to 100 | up to 100 | up to 100 |
| 2. | Propylene glycol | 5.0 | 5.0 | 5.0 | 5.0 |
| 3. | Liquid paraffin | 40.0 | 40.0 | 40.0 | 40.0 |
| 4. | Polyethoxylated vitamin E(E.O. = 10) | 3.0 | 3.0 | — | — |
| 5. | Polyoxyethylene(20) sorbitan monostearate | — | — | 1.8 | 1.8 |
| 6. | Sorbitan sesquioleate | — | — | 1.2 | 1.2 |
| 7. | Vitamin E | 0.2 | — | 0.2 | — |
| 8. | Skim milk | 1.0 | 1.0 | 1.0 | 1.0 |
| | Viscosity(cps) | ~50 | ~40 | ~50 | ~40 |

EXPERIMENTAL EXAMPLE 1

In order to examine stability of the emulsions during the storage, the emulsions obtained in Examples 1 to 2 and Comparative examples 1 to 2 were stored at 0° C., 30° C. and 50° C. and the degree of phase separation of the emulsions were examined after 1 week, 1 month and 3 months, respectively. The results are shown in Table 2.

TABLE 2

| Temp. & Term | | Example | | | |
|---|---|---|---|---|---|
| | | Ex. 1 | Ex. 2 | Comp.Ex.1 | Comp.Ex.2 |
| 50° C. | 1 week | O | O | O | O |
| | 1 month | O | O | X | X |
| | 3 months | O | O | XX | XX |
| 30° C. | 1 week | O | O | O | O |
| | 1 month | O | O | O | O |
| | 3 months | O | O | X | X |
| 0° C. | 1 week | O | O | O | O |
| | 2 month | O | O | X | X |
| | 6 months | O | O | X | X |

Note
O: No phase separation
X: Slight phase separation
XX: Complete phase separation As can be seen from Table 2, the emulsions of Examples 1 to 2, which contain polyethoxylated vitamin E, are stable without any phase separation even after storage at 50° C. for 3 months and at 0° C. for 6 months, while the emulsions of Comparative examples 1 and 2 which contain conventional emulsifiers and does not contain polyethoxylated vitamin E, undergoes phase separation.

EXPERIMENTAL EXAMPLE 2

In order to observe skin irritation which may be caused by a prolonged use of compositions according to the invention, the formulations in Examples 1 to 2 and Comparative examples 1 to 2 were applied on the upper arm of 50 females aging 20 to 30 years and the "closed patch test" was carried out. Irratible response was calculated and the results are shown in Table 3.

TABLE 3

| Sample | Time Irritation Response(n = 50) | | |
|---|---|---|---|
| | 4 Hours | 48 Hours | Average |
| Example 1 | 0 | 0 | 0 |
| Example 2 | 0 | 0 | 0 |
| Comp. Ex. 1 | 0.4 | 0 | 0.2 |
| Comp. Ex. 2 | 0.5 | 0 | 0.25 |

As can be seen from Table 3, the emulsions according to the invention cause no skin irritation after application for 48 hours under closed condition.

EXPERIMENTAL EXAMPLE 3

4 Groups each consisting of 40 females aging 20 to 40 years were applied on their face every day for 20 days with emulsions of Examples 1 to 2 and Comparative examples 1 to 2, respectively and counted the number of subjects who feel the conditions of their face more better than before using the emulsion in terms of smoothness, moisture and softness. The results are shown in Table 4.

TABLE 4

| Item | Ex. No. | | | |
|---|---|---|---|---|
| | Example 1 | Example 2 | Comp. Ex. 1 | Comp. Ex. 2 |
| Smoothness | 25 | 22 | 23 | 18 |
| Moisture | 30 | 25 | 22 | 18 |
| Softness | 32 | 25 | 22 | 20 |

As can be seen from Table 4, the emulsions according to the invention more moisturize and soften the skin and impart skin with improved smoothness compared with the comparative emulsion without polyethoxylated vitamin E.

EXPERIMENTAL EXAMPLE 4

In order to examine the cell protecting action of the combination polyethoxylated vitamin E and milk, a photohemolysis test was carried out as follows:

Blood collected from healthy men aging 20 to 30 years was centrifuged at 8000 rpm for 5 minutes and erythrocytes are diluted with physiological saline buffer to give an erythrocyte suspension. 5 Pyrex test tubes of 1.0 cm diameter were prepared and each was charge with 4 ml of the suspension. To one of the test tubes was added 50 μl of ethanol as a control and to the remaining 4 tubes were added 50 μl of the sample. 5 tubes were preincubated in the dark for 30 minutes.

After completion of preincubation, 50 μl of 80 μM hematoporphyrin as a photosensitizer was added and the end of the tube was sealed with a paraffin film. In the center of a 50×20×25 cm rectangular hexahedron box, the inside of which had been painted black, was placed a 20 W fluorescent lamp. The tubes were located at points 5 cm distant from the lamp and were irradiated for 15 minutes.

After completion of irradiation, the transmittances of each test tubes kept in the dark at 700 nm were measured at intervals of 15 minutes. The increase in the transmittance of the suspension at this wavelength was proportional to the degree of hemolysis.

Every steps of the above expreiment was carried out in a room, the temperature of which was maintained to 27° C. The cell protecting activity of the sample against active oxygen species was defined as the time(minutes) required for hemolyzing 50% of the erythrocytes under the above measurement conditions. The results are shown in Table 5.

TABLE 5

| Sample | Cell protecting activity(Min) |
|---|---|
| Example 1 | 168 |
| Example 2 | 88 |
| Comp. Example 1 | 126 |
| Comp. Example 2 | 59 |
| Control | 52 |

As shown in Table 5, the emulsions containing milk and polyethoxylated vitamin E showed higher cell protecting action and particularly, the emulsion of Example 1, which contains milk, polyethoylated vitamin E and vitamin E exhibited the highest cell protecting action.

Polyethoxylated vitamin E is also useful to formulate various emulsions such as body lotions, massage oils, sun-screen lotions as well as milky lotion.

Hereinafter, formulations containing milk plus polyethoxylated vitamin E are illustrated.

Formulation 1: Milky lotion

| Components | Parts by weight |
|---|---|
| Liquid paraffin | 40 |
| Polysiloxan | 0.1 |
| Polyethoxylated Vitamin E(E.O = 10) | 3.0 |
| Vitamin E acetate | 0.1 |
| Methyl paraben | 0.1 |
| Propyl paraben | 0.1 |
| Sterilized milk | 1.0 |
| Distilled water | up to 100 |

Formulation 2: Body lotion

| Components | Parts by weight |
|---|---|
| Liquid paraffin | 8.0 |
| Stearyl alcohol | 2.0 |
| Polyethoxylated Vitamin E(E.O = 15) | 2.0 |
| Polyethoxylated Vitamin E(E.O = 5) | 2.0 |
| Silicone oil | 0.1 |
| Tocopherol | 0.1 |
| 1,3-Butylene glycol | 1.0 |
| Methyl paraben | 0.1 |
| Sterilized milk | 5.0 |
| Imidazolinyl urea | 0.1 |
| Perfume | 0.1 |
| Distilled water | up to 100 |

Formulation 3: Massage oil

| Components | Parts by weight |
|---|---|
| Liquid paraffin | 10.0 |
| Isopropyl myristate | 2.0 |
| Polyethoxylated Vitamin E(E.O = 13) | 2.5 |
| Polyethoxylated Vitamin E(E.O = 6) | 1.8 |
| Carboxy vinyl polymer | 0.4 |
| Caustic soda(in 10% solution) | 0.4 |
| Skim milk | 1.5 |
| Tocopheryl acetate | 0.1 |
| Imidazolinyl urea | 0.2 |
| Perfume | 0.1 |
| Distilled water | up to 100 |

Formulation 4: Sun-screen lotion

| Components | Parts by weight |
|---|---|
| Liquid paraffin | 10.0 |
| Isopropyl myristate | 2.0 |
| Homosalate | 8.0 |
| Polyethoxylated Vitamin E(E.O = 15) | 0.5 |
| Silicone oil | 0.1 |
| Tocopherol | 0.5 |
| Carboxy vinyl polymer | 0.15 |
| Triethanolamine | 1.2 |
| Whole milk | 2.0 |
| Methyl paraben | 0.1 |
| Imidazolinyl urea | 0.1 |
| Perfume | 0.1 |
| Distilled water | up to 100 |

What is claimed is:

1. An oil-in-water cosmetic emulsion composition comprising an effective amount of oil, an effective amount of milk and as an emulsifier polyethoxylated vitamin B in an amount of 0.01 to 10.0% by weight based on the total weight of the emulsion, said polyethoxylated vitamin E having 5 to 15 moles of ethylene oxide in the molecule, wherein the weight ratio of polyethoxylated vitamin E to milk is 1:1 to 1:10 in parts and wherein the emulsion has a viscosity of less than 100 cps.

2. The O/W emulsion claimed in claim 1, which further comprises vitamin E or vitamin E acetate in amount of 0.01 to 10% by weight.

3. The O/W emulsion as claimed in claim 1, wherein the milk is powdered whole milk, powdered skim milk, whole milk or sterilized whole milk.

4. The O/W emulsion as claimed in claim 1, containing 0.1 to 1% by weight of said emulsifier.

* * * * *